US008348986B2

(12) United States Patent
Choi et al.

(10) Patent No.: US 8,348,986 B2
(45) Date of Patent: Jan. 8, 2013

(54) PHOTOSTIMULATION APPARATUS (75) Inventors: Jee Hyun Choi, Seoul (KR); Guk Bae Kim, Seoul (KR); Hee Sup Shin, Gyeonggi-do (KR); Ho Kun Sung, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 671 days.

(21) Appl. No.: 12/551,613

(22) Filed: Sep. 1, 2009

(65) Prior Publication Data

US 2010/0249890 A1   Sep. 30, 2010

(30) Foreign Application Priority Data

Mar. 25, 2009   (KR) ......................... 10-2009-0025521

(51) Int. Cl.
*A61N 5/06* (2006.01)
(52) U.S. Cl. ................ 607/92; 607/90; 607/89; 607/88; 606/14; 606/13; 606/2
(58) Field of Classification Search ................ 607/92, 607/90, 89, 88; 606/14, 13, 2
See application file for complete search history.

(56) References Cited

U.S. PATENT DOCUMENTS 5,766,234 A * 6/1998 Chen et al. ....................... 607/92
5,999,847 A   12/1999 Elstrom 2002/0138120 A1 * 9/2002 Whitehurst ..................... 607/88
2002/0147464 A1   10/2002 Peyman
2007/0032846 A1   2/2007 Ferren et al.

FOREIGN PATENT DOCUMENTS

| EP | 1074275 A1 | 2/2001 |
|---|---|---|
| JP | H11507284 | 6/1999 |
| KR | 10-0191230 | 6/1999 |
| WO | WO 2005/037372 A1 | 4/2005 |
| WO | WO 2007/106856 A2 | 9/2007 |
| WO | WO 2008/046015 A1 | 4/2008 |

OTHER PUBLICATIONS

Japanese Patent Office Action corresponding to Patent Application No. 2009-211785 dated Dec. 20, 2011.
European Search Report corresponding to European Patent No. EP 09 29 0736 dated Jun. 28, 2010.
Office Action dated Mar. 14, 2011 corresponding to the Korean Patent Application No. 10-2009-0025521 (w/translation).

* cited by examiner

*Primary Examiner* — Kinam Park
(74) *Attorney, Agent, or Firm* — Ohlandt, Greeley, Ruggiero & Perle, L.L.P.

(57) ABSTRACT

A photostimulation apparatus may include: a membrane for insertion into a living body; and at least one cell disposed on the membrane. Each cell may include a first light source for irradiating light to a photosensitive material in the living body. Further, a photostimulation apparatus may include: a membrane for insertion into a living body; and at least one first light source disposed on the membrane for irradiating light to a photosensitive material in the living body. Since the photostimulation apparatus is placed on the surface of cortex or dura, it may minimize damage of the brain tissue and may activate and/or inhibit a large area simultaneously using light.

9 Claims, 6 Drawing Sheets

PHOTOSTIMULATION APPARATUS

CROSS-REFERENCE TO RELATED APPLICATIONS

This application claims priority to Korean Patent Application No. 10-2009-0025521, filed on Mar. 25, 2009, and all the benefits accruing therefrom under 35 U.S.C. §119, the contents of which in its entirety are herein incorporated by reference.

BACKGROUND OF THE INVENTION

1. Field

A photostimulation apparatus is disclosed.

2. Description of the Related Art

Recently, light-sensitive proteins activating or inhibiting nerve cells in response to light with specific wavelength have been developed in the field of brain study. Using the light-sensitive proteins, it is possible to control the nerve cells in the neural circuitry more freely and elaborately. With the conventional electrical microstimulation using a micro-stimulant, target nerve cells can be activated only. For the study of the neural circuitry, it is required to stimulate specific cells and to measure response from nerve cells in other area resulting from the inter-connection inside the neural circuitry, at the same time. With an artificial electrical stimulation, it is difficult to measure the subtle electrical physiological response from other cells because of noise.

In contrast, with photostimulation, the target nerve cells can be selected freely through selection of promoters. Once light-sensitive proteins are expressed in the target nerve cells, both activation and inhibition can be controlled freely by controlling the wavelength of photostimulation. Accordingly, with photostimulation, the neural circuitry can be studied more elaborately and systematically. Moreover, it may be helpful in studying how a specific neuropsychiatric disease is connected with specific brain nerve cells and how it causes problems in the neural circuitry, as well as in treating the disease. Especially, in clinical practice, whereas the conventional deep brain stimulation technique allows only activation of nerve cells through electrical stimulation, the photostimulation technique allows both activation and inhibition. Hence, it may provide an epoch-making turning point in the treatment of neuropsychiatric diseases.

The cerebral cortex of the human brain is a region that plays a key role in memory, attention, perceptual awareness, thought, language, and consciousness. It constitutes the outermost layer of the cerebrum. The functions of the areas of the cerebral cortex are well known. Located right beneath the skull, the cerebral cortex may be easily damaged by accidents or diseases. On the other hand, accessibility to treatment is relatively high because it is located at the outer side of the brain. Therefore, the cerebral cortex makes a good target for neural photostimulation.

SUMMARY OF THE INVENTION

A photostimulation apparatus may be provided which may activate and/or inhibit nerve cells in the living body by irradiating light on a large area. The apparatus may further inject a photosensitive material into the living body without insertion into the living body.

According to an aspect of the invention, a photostimulation apparatus may include: a membrane for insertion into a living body; and at least one cell disposed on the membrane. Each cell may include a first light source for irradiating light to a photosensitive material in the living body.

According to another aspect of the invention, a photostimulation apparatus may include: a membrane for insertion into the living body; and at least one first light source disposed on the membrane for irradiating light to a photosensitive material in the living body.

Using the photostimulation apparatuses, the processes of injecting photosensitive material into the living body, irradiating light to the injected photosensitive material, and measuring an electrical signal from the living body for verification of photostimulation may be carried out with a single apparatus. Hence, the number of surgical operations on the living body may be reduced.

Further, since the apparatus is placed on the surface of cortex or dura, damage to the brain tissue may be minimized and a large area may be activated and/or inhibited simultaneously using light. Accordingly, it may be effectively utilized in the study of the brain, treatment of neuropsychiatric diseases, or the like.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Figure 1A:
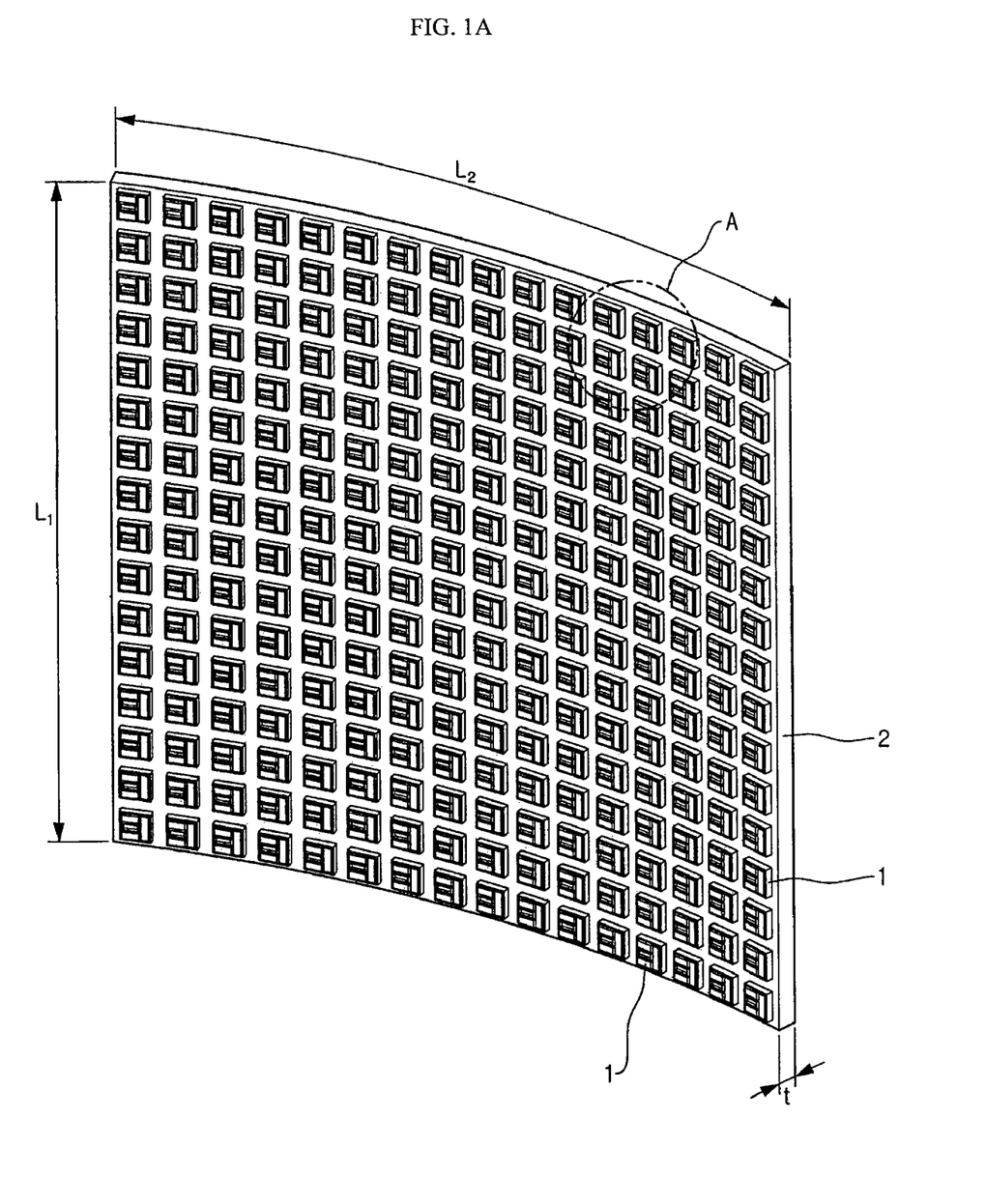
FIG. 1A is a perspective view of a photostimulation apparatus according to an exemplary embodiment.
Figure 1B:
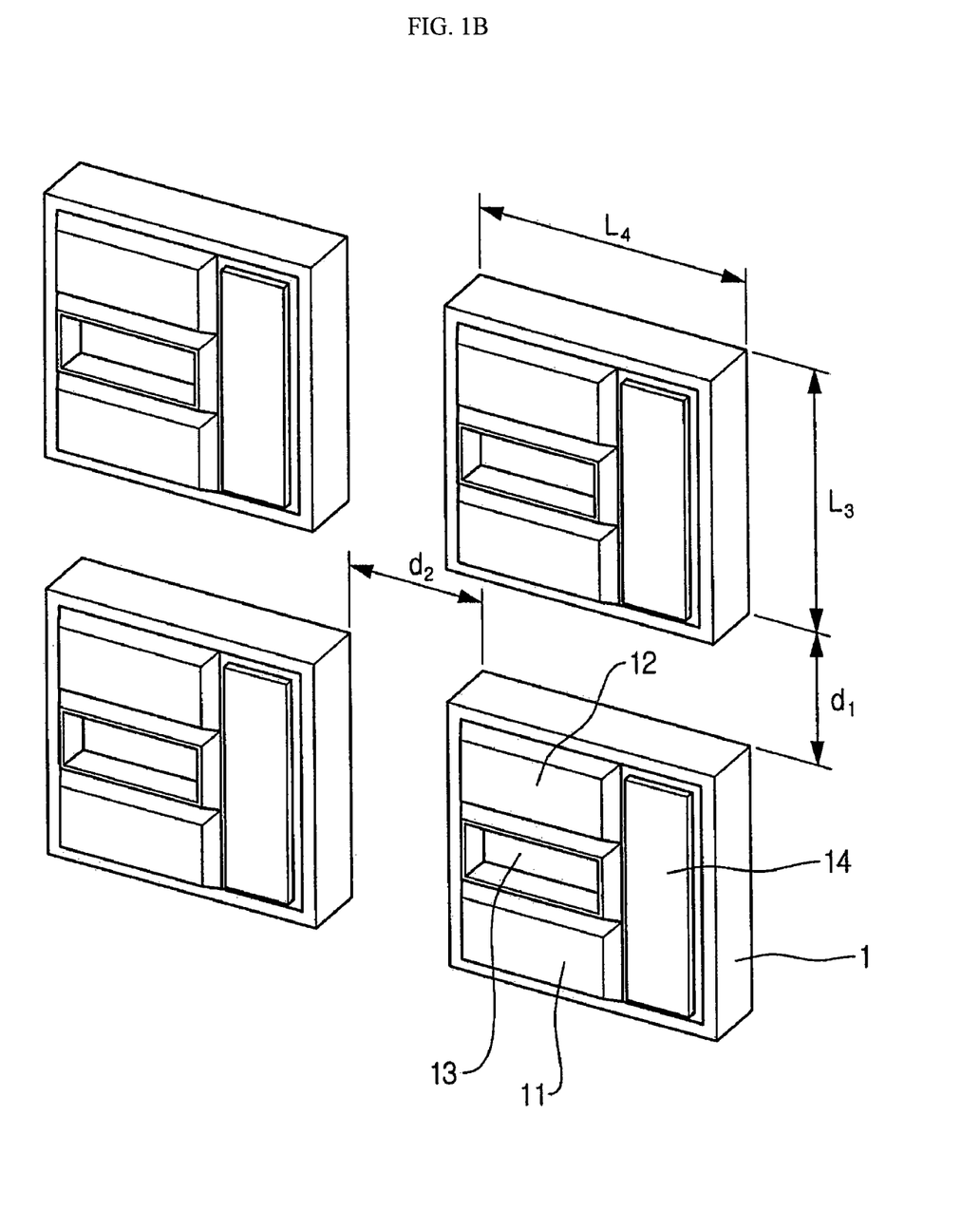
FIG. 1B is an enlarged perspective view of the region A in FIG. 1A.

FIG. 1A is a perspective view of a photostimulation apparatus according to an exemplary embodiment, and FIG. 1B is an enlarged perspective view of the region A in FIG. 1A.

Referring to FIGS. 1A and 1B, a photostimulation apparatus may include a membrane 2 and at least one cell 1 disposed on the membrane 2. The photostimulation apparatus may be used as inserted at a location relatively close to the brain of a living body such as human or animals.

The membrane 2 may be prepared to have a dimension and a thickness appropriate for insertion into the living body by means of nanofabrication. For example, the membrane 2 may have a thickness t of about 1 mm or smaller. The membrane 2 may also have a thickness t of about 100 μm (micrometers) or smaller. Further, the membrane 2 may have a dimension of about 300 mm or smaller. As used herein, the dimension means the longest spatial length of an entity. For a polygon, the dimension may mean the length of the largest side. For an ellipse, the dimension may mean the major axis. For example, the membrane 2 may have the shape of a rectangular plate, with sides $L_1$, $L_2$ about 300 mm or smaller. The length of the sides $L_1$, $L_2$ may be the same or different. In another exemplary embodiment, the membrane 2 may have the shape of a disc or may have other different shapes.

The membrane 2 may be made of an organic material or an inorganic material. Further, the membrane 2 may be made of a flexible material so that it may be bent depending on the brain's motions. For example, the membrane 2 may be made of polyimide, polydimethylsiloxane (PDMS), or other suitable materials.

The at least one cell 1 may be disposed on the membrane 2. In an exemplary embodiment, each cell 1 may have the shape of a rectangular plate, with sides $L_3$, $L_4$ about 5 mm or smaller. The length of the sides $L_3$, $L_4$ may be the same or different. The at least one cell 1 may be arranged regularly or irregularly.

In an exemplary embodiment, the at least one cell 1 may include a plurality of cells 1 arranged in arrays. For example, the plurality of cells may be arranged in an array having the shape of a rectangular lattice. The plurality of cells 1 may be spaced apart from each other by distances $d_1$, $d_2$ in the transverse and longitudinal directions, respectively. For example, the distances $d_1$, $d_2$ between the plurality of cells 1 may be about 1 mm or smaller. The distances $d_1$, $d_2$ in the transverse and longitudinal directions may be the same or different. Since each cell 1 is spaced apart from each other, the membrane 2 may be folded or bent at the portion where the cells 1 are spaced apart from each other. As a result, the whole photostimulation apparatus may be bent according to the contour or motion of the brain.

The shape of the array of the plurality of cells 1 shown in FIGS. 1A and 1B are only exemplary. In other exemplary embodiments, the array may have a circular shape or may have other different shapes. Alternatively, the at least one cell 1 may be arranged on the membrane 2 irregularly.

Further, the shape of the cell 1 illustrated in FIGS. 1A and 1B are only exemplary. In other exemplary embodiments, the cell 1 may have the shape of a polyhedron different from those in FIGS. 1A and 1B or a curved figure. Each cell 1 may be formed by laminating a material on the membrane 2. Alternatively, the cell may refer to a region formed on the membrane 2 by forming a light source or the like on the membrane 2, which will be described later.

Each of the at least one cells may irradiate light with a specific wavelength to a photosensitive material in the living body in which the photostimulation apparatus is inserted to activate and/or inhibit the nerve cells in which the photosensitive material are expressed. Further, each cell 1 may detect the behavior of the brain nerve cells in response to the irradiation of light to the photosensitive material. In addition, the photosensitive material may be injected into the living body using each cell 1.

The photosensitive material forms ion channels or ion pumps in the nerve cell which activate or inhibit the nerve cell by passing cations or anions into the nerve cell in response to the irradiated light. The photosensitive material may be, for example, ion channels/pumps and receptors chemically modified in response to light, naturally occurring photosensitive proteins, or the like.

The ion channel and receptor modified in response to light may have a structure in which a photoswitch is attached or injected adjacent to the receptor. For example, the ion channel may be a Shaker potassium channel. And, the receptor may be an ionic glutamate receptor (e.g. iGluR6) gated by light. The photoswitch may have an azobenzene group isomerized by light and, for example, may have a structure in which a potassium channel antagonist and an iGluR6 agonist are covalently bonded. By irradiating light with a specific wavelength, e.g. about 460 nm (nanometers), to the ion channel and receptor, a nerve cell may be activated, thereby generating an electrical signal. On the contrary, by irradiating light with a specific wavelength, e.g. about 580 nm (nanometers), the generation of the electrical signal from the nerve cell may be inhibited.

The photosensitive protein is based on rhodopsin which isomerizes when light with a specific wavelength is irradiated. For example, it may include the multiple-component *Drosophila* sp. visual system rhodopsin cascade (ChArGe), channelrhodopsin-2 (ChR2), or the like. By irradiating light with a specific wavelength to the photosensitive protein, e.g. light with a wavelength of about 460 nm (nanometers) for ChR2, the photosensitive protein may be activated to allow flow of cations into the nerve cell, thereby resulting in activation of the nerve cell.

For this purpose, each cell 1 may include a first light source 11. The first light source 11 may irradiate light with a specific wavelength for activating or inhibiting the nerve cell by means of the photosensitive material. For example, for activation of the nerve cell, the first light source 11 may irradiate light with a wavelength shorter than about 500 nm (nanometers). On the contrary, for inhibition of the nerve cell, the first light source 11 may irradiate light with a wavelength of about 500 nm (nanometers) or longer.

In an exemplary embodiment, each cell 1 may further include a second light source 12 in addition to the first light source 11. The first light source 11 and the second light source 12 may irradiate light with different wavelengths. For example, the first light source 11 may irradiate light with a wavelength shorter than about 500 nm (nanometers), and the second light source 12 may irradiate light with a wavelength of about 500 nm (nanometers) or longer. Accordingly, the nerve cell may be activated using the first light source 11 and, at the same time, the nerve cell may be inhibited using the second light source 12.

The first light source 11 and the second light source 12 may be an organic light-emitting element or an inorganic light-emitting element. For example, the first light source 11 and the second light source 12 may be an organic light-emitting element such as an organic light-emitting diode (OLED) or an inorganic light-emitting element such as a light-emitting diode (LED), laser diode (LD) and vertical-cavity surface-emitting laser (VCSEL).

In an exemplary embodiment, each cell 1 may further include an injector 13 for injecting the photosensitive material into a living body. By injecting the photosensitive material into the living body using the injector 13 and irradiating light to the injected photosensitive material using the first and second light sources 11, 12, the nerve cell may be activated and/or inhibited by means of the photosensitive material. The injector 13 may be linked to a channel, valve, etc. through which the photosensitive material is transferred. Further, for control of the injection volume of the photosensitive material, the injector 13 may be connected to a micro dispenser, micro multiplexer, or the like.

In an exemplary embodiment, each cell 1 may further include an electrode 14 which detects an electrophysiological signal from the nerve cell activated or inhibited as light is irradiated by the first and second light sources 11, 12 to the photosensitive material. The electrode 14 may be made of a conducting material such as metal. By detecting an electrical signal using the electrode 14, the activation and/or inhibition of the nerve cell in the living body may be monitored. Further, in an exemplary embodiment wherein a plurality of cells 1 are arranged on the membrane 2 in arrays, the electrical signal can be detected from a larger area.

The arrangement of the first and second light sources 11, 12, the injector 13 and the electrode 14 in the cell 1, and the arrangement of the cells 1 on the membrane 2 illustrated in FIGS. 1A and 1B are only exemplary. In other exemplary embodiments, the arrangements may be different from those illustrated in FIGS. 1A and 1B.

Figure 2A:
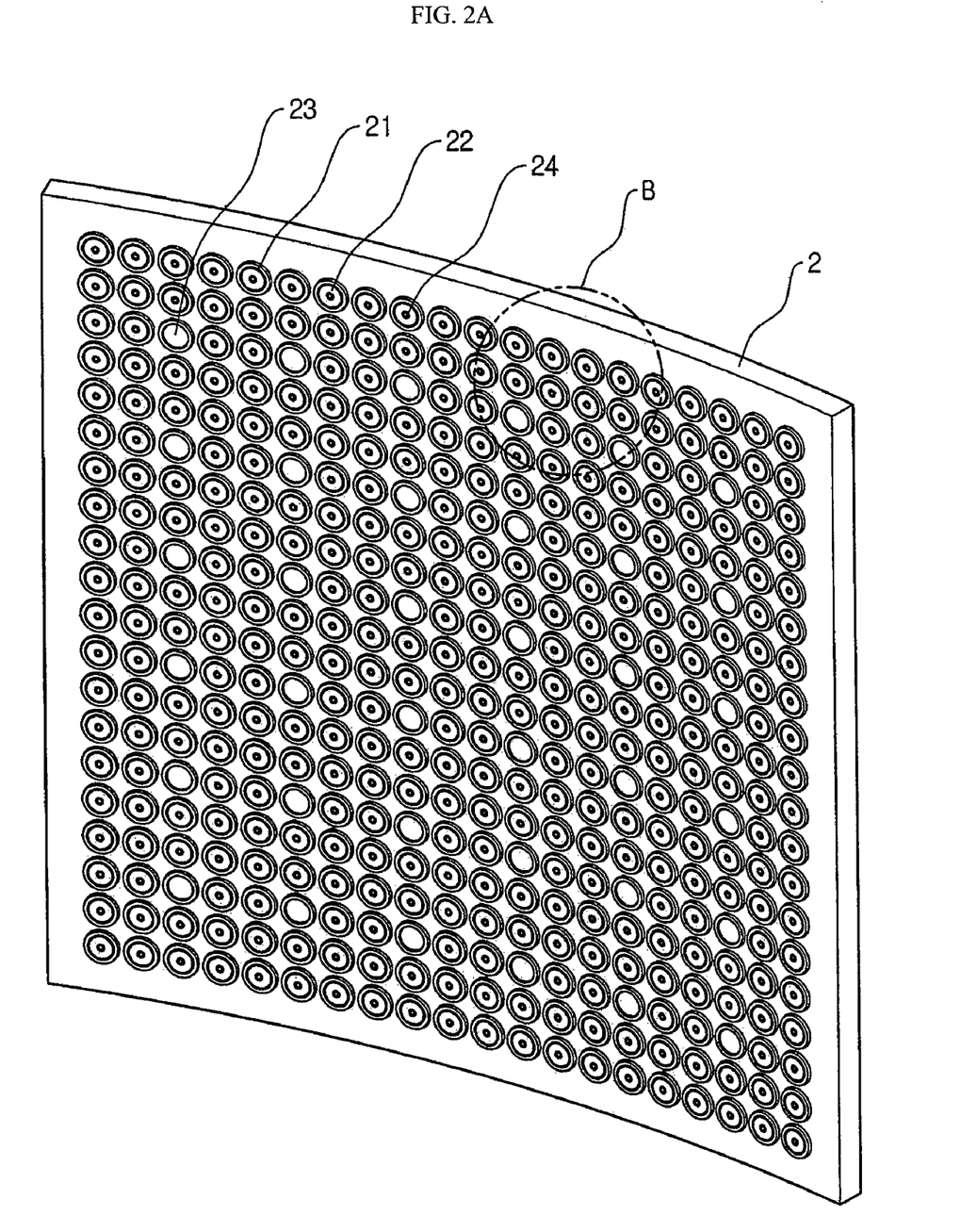
FIG. 2A is a perspective view of a photostimulation apparatus according to another exemplary embodiment.
Figure 2B:
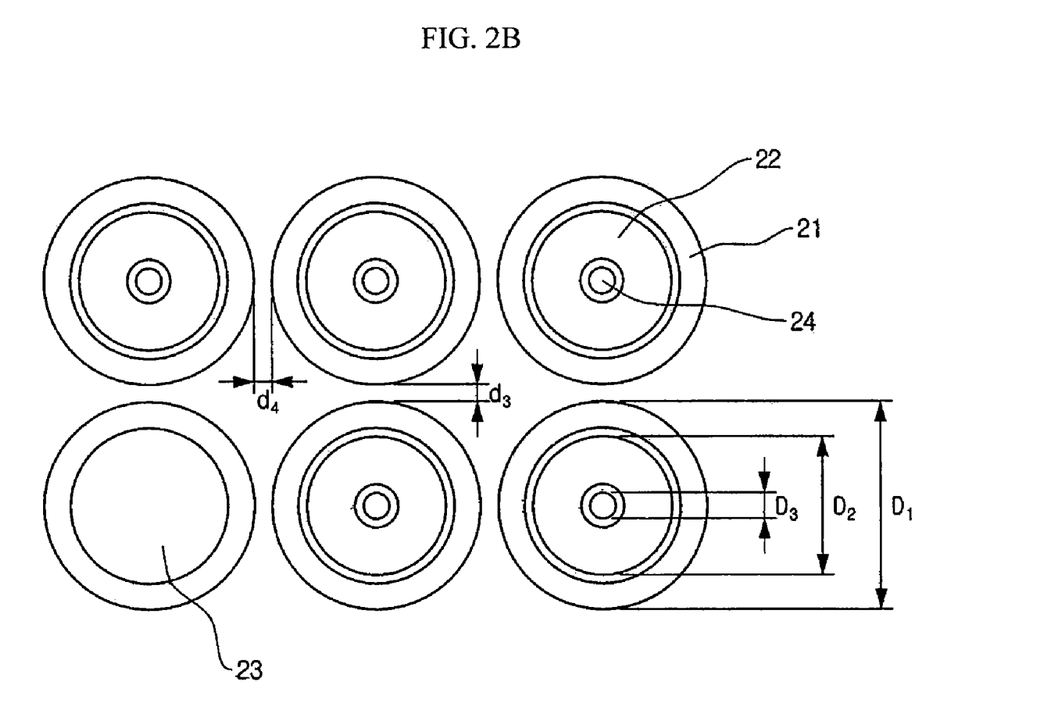
FIG. 2B is an enlarged perspective view of the region B in FIG. 2A.

FIG. 2A is a perspective view of a photostimulation apparatus according to another exemplary embodiment, and FIG. 2B is an enlarged perspective view of the region B in FIG. 2A.

Referring to FIGS. 2A and 2B, a photostimulation apparatus may include a membrane 2 and at least one first light source 21 disposed on the membrane 2. The photostimulation apparatus may be used as inserted at a location relatively close to the brain of a living body such as human or animals. The configuration and function of the membrane 2 are the same as those of the above exemplary embodiment described referring to FIGS. 1A and 1B. Therefore, a detailed description thereof will be omitted.

The at least one first light source 21 may be disposed on the membrane 2. Each first light source 21 may have the shape of a hollow disc. In an exemplary embodiment, the first light source 21 may have a diameter $D_1$ of about 5 mm or smaller. The at least one first light source 21 may be arranged regularly or irregularly.

In an exemplary embodiment, a plurality of the first light sources 21 may be arranged in arrays. For example, the plurality of the first light sources 21 may be arranged in an array having the shape of a rectangular lattice. At this time, each first light source 21 may be spaced apart from each other by distances $d_3$, $d_4$ in the transverse and longitudinal directions, respectively. For example, the distances $d_3$, $d_4$ between the plurality of first light sources 21 may be about 1 mm or smaller. The distances $d_3$, $d_4$ in the transverse and longitudinal directions may be the same or different. The whole photostimulation apparatus may be bent according to the contour or motion of the brain as the membrane 2 is folded or bent at the portion where the first light sources 21 are spaced apart from each other.

The shape of the array of the plurality of first light sources 21 shown in FIGS. 2A and 2B are only exemplary. In other exemplary embodiments, the array may have a circular shape or may have other different shapes. Alternatively, the at least one first light source 21 may be arranged on the membrane 2 irregularly.

The first light source 21 may irradiate light with a specific wavelength for activating or inhibiting the nerve cell by means of a photosensitive material. For example, for activation of the nerve cell, the first light source 21 may irradiate light with a wavelength shorter than about 500 nm (nanometers). On the contrary, for inhibition of the nerve cell, the first light source 21 may irradiate light with a wavelength of about 500 nm (nanometers) or longer.

In an exemplary embodiment, at least one injector 23 may be further disposed on the membrane 2. Further, a plurality of the injectors 23 may be arranged in arrays. For example, the plurality of injectors 23 may be arranged in an array having a shape identical to that of the array of the plurality of first light sources 21. The plurality of injectors 23 may be arranged such that one or more of the first light sources 21 are positioned between each injector 23. In other words, in an array of the plurality of first light sources 21, the injector 23 may be positioned replacing the first light source 21 with a specific interval. In another exemplary embodiment, the plurality of injectors 23 and the plurality of first light source 21 may be arranged in arrays having different shapes.

By injecting the photosensitive material into the living body using the injector 23 and irradiating light to the injected photosensitive material using the first light source 21, the nerve cell may be activated and/or inhibited by means of the photosensitive material. For injection of the photosensitive material, the injector 23 may be linked to a channel, valve, etc. through which the photosensitive material is transferred. Further, for control of the injection volume of the photosensitive material, the injector 23 may be connected to a micro dispenser, micro multiplexer, or the like.

In an exemplary embodiment, a second light source 22 may be positioned in each of the at least one first light source 21. Since each first light source 21 has the shape of a hollow disc, the second light source 22 may be positioned in the hollow area of the disc. For example, if the first light source 21 has a diameter $D_1$ of about 180 μm (micrometers), the second light source 22 positioned in the first light source 21 may have a diameter $D_2$ of about 128 μm (micrometers) or smaller.

The first light source 21 and the second light source 22 may irradiate light with different wavelengths. For example, the first light source 21 may irradiate light with a wavelength shorter than about 500 nm (nanometers), and the second light source 22 may irradiate light with a wavelength of about 500 nm (nanometers) or longer. Accordingly, the nerve cell may be activated using the first light source 21 and, at the same time, the nerve cell may be inhibited using the second light source 22.

The first light source 21 and the second light source 22 may be an organic light-emitting element or an inorganic light-emitting element. For example, the first light source 21 and the second light source 22 may be an organic light-emitting element such as an OLED or an inorganic light-emitting element such as an LED, LD and VCSEL.

In an exemplary embodiment, the at least one second light source 22 may have the shape of a hollow disc, and an electrode 24 may be positioned in each second light source 22. For example, if the second light source 22 has a diameter $D_2$ of about 128 μm (micrometers), the electrode 24 positioned in the second light source 22 may have a diameter $D_3$ of about 20 μm (micrometers) or smaller. The electrode 24 may detect an electrical signal generated from the nerve cell as light is irradiated to the photosensitive material by the first and second light sources 21, 22. The electrode 24 may be made of a conducting material such as metal. By detecting the electrical signal using the electrode 24, the activation and/or inhibition of the nerve cell may be monitored.

Figure 3A:
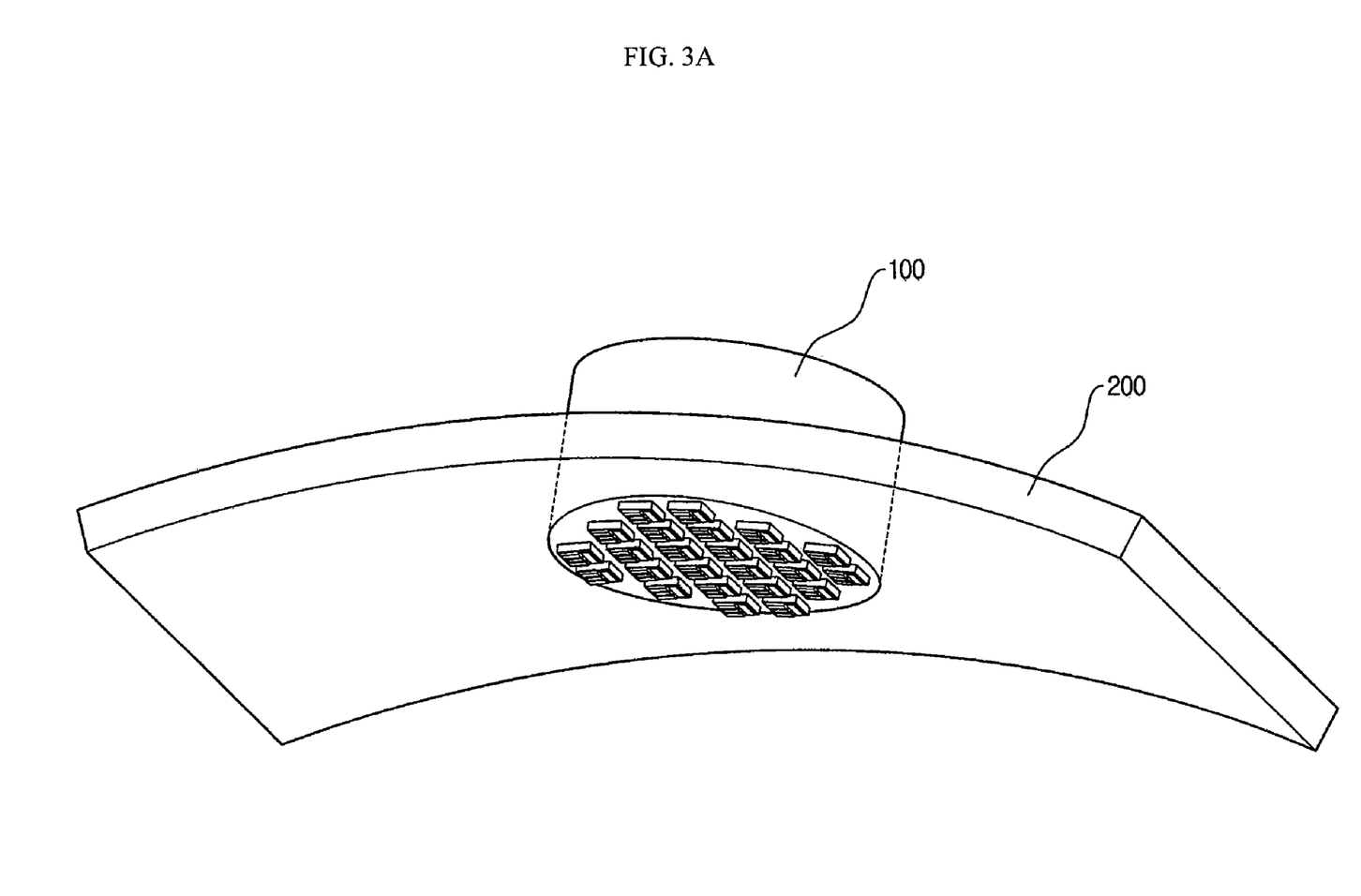
FIG. 3A is a schematic view of a photostimulation apparatus according to an exemplary embodiment inserted into the human body.

FIG. 3A is a schematic view of a photostimulation apparatus according to an exemplary embodiment inserted into the human body.

Referring to FIG. 3A, a hole penetrating the human skull 200 may be formed on a portion of the skull 200, and a photostimulation apparatus 100 may be positioned in the hole. Since the photostimulation apparatus 100 exposed through the hole below is located close to the brain, injection of a photosensitive material, irradiation of light to the photosensitive material, or detection of an electrical signal emitted from the nerve cell by means of the photosensitive material, or the like are possible.

Figure 3B:
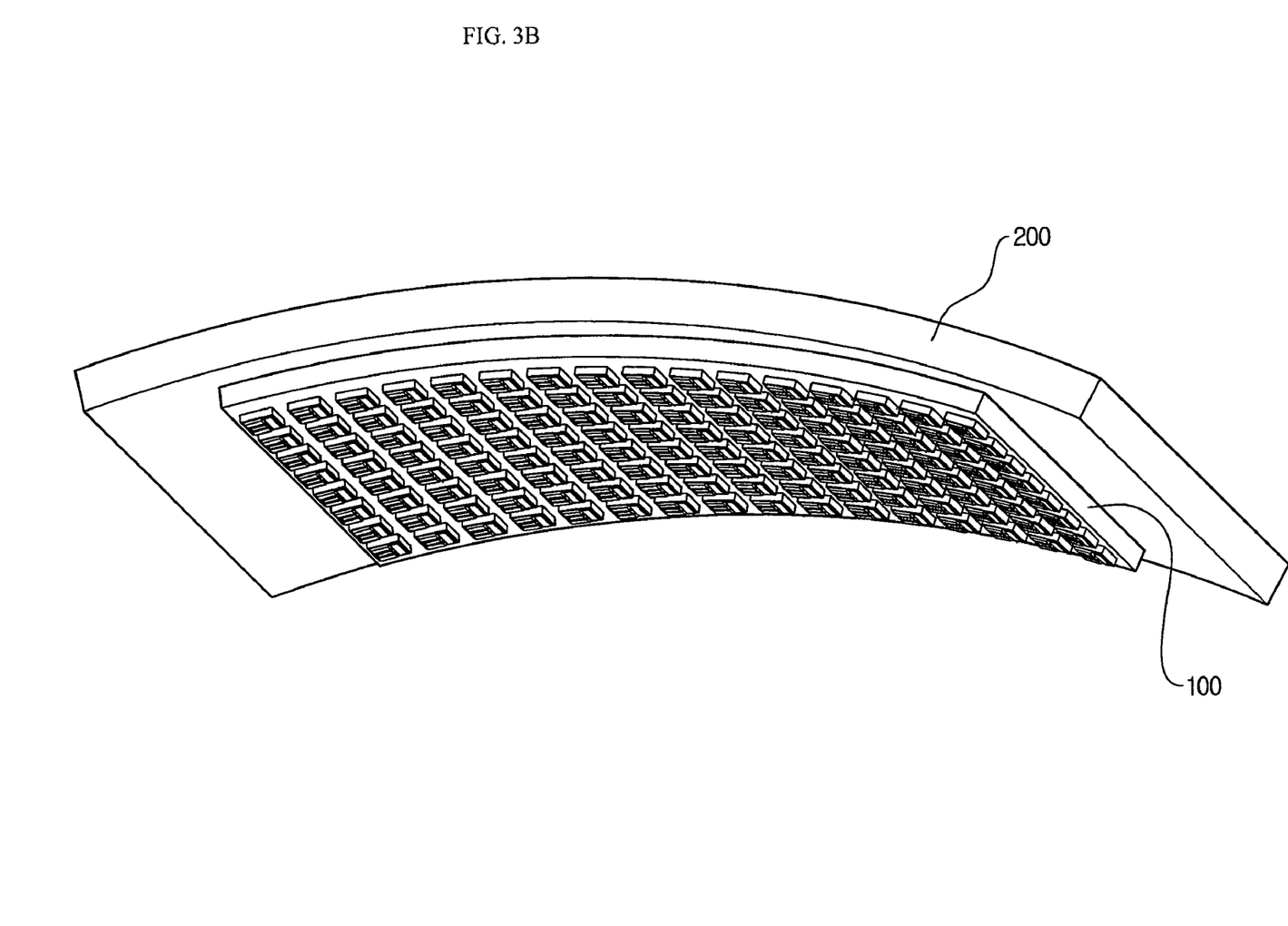
FIG. 3B is a schematic view of a photostimulation apparatus according to another exemplary embodiment inserted into the human body.

FIG. 3B is a schematic view of a photostimulation apparatus according to another exemplary embodiment inserted into the human body.

Referring to FIG. 3B, a photostimulation apparatus 100 may be inserted beneath the human skull 200. That is, the photostimulation apparatus 100 may be located between the skull 200 and the brain. In this case, a portion of the skull 200 may be made thinner by peeling and the photostimulation apparatus 100 may be located at the thin portion of the skull 200. As a result, the whole photostimulation apparatus 100 may be located close to the brain, and a relatively larger area may be activated and/or inhibited using light.

While the exemplary embodiments have been shown and described, it will be understood by those skilled in the art that various changes in form and details may be made thereto without departing from the spirit and scope of this disclosure as defined by the appended claims. In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A photostimulation apparatus comprising:
a membrane for insertion into a living body; and
at least one cell disposed on the membrane,
wherein each of the at least one cell comprises first and second light sources for irradiating light to a photosensitive material in the living body,
wherein the first light source can activate nerve cells in the living body by irradiating light with a first wavelength to the photosensitive material, and
wherein the second light source can inhibit the nerve cells by irradiating light with a second wavelength different from the first wavelength to the photosensitive material.

2. The photostimulation apparatus according to claim 1, wherein the first light source and the second light source comprise any one of an organic light-emitting diode, a light-emitting diode, a laser diode and a vertical-cavity surface-emitting laser.

3. The photostimulation apparatus according to claim 1, wherein each of the at least one cell further comprises an injector for injecting the photosensitive material to the living body.

4. The photostimulation apparatus according to claim 1, wherein each of the at least one cell further comprises an electrode for detecting an electrical signal from the living body.

5. The photostimulation apparatus according to claim 1, wherein the membrane has a thickness of about 1 mm or smaller.

6. The photostimulation apparatus according to claim 1, wherein each of the at least one cell has a dimension of about 5 mm or smaller.

7. The photostimulation apparatus according to claim 1, wherein the at least one cell comprises a plurality of cells spaced apart from each other.

8. The photostimulation apparatus according to claim 7, wherein the membrane has a curved surface.

9. The photostimulation apparatus according to claim 1, wherein the at least one cell comprises a plurality of cells arranged in arrays.

* * * * *